(12) United States Patent
Phillips

(10) Patent No.: US 6,273,722 B1
(45) Date of Patent: Aug. 14, 2001

(54) HYBRID PRESS FIT-THREADED DENTAL IMPLANT

(75) Inventor: Carol L. Phillips, San Luis Obispo, CA (US)

(73) Assignee: Swiss Implants, Inc., San Luis Obispo, CA (US)

( * ) Notice: Subject to any disclaimer, the term of this patent is extended or adjusted under 35 U.S.C. 154(b) by 0 days.

(21) Appl. No.: 09/449,873

(22) Filed: Nov. 29, 1999

(51) Int. Cl.$^7$ ................................................. A61C 8/00
(52) U.S. Cl. ...................................... 433/174; 433/173
(58) Field of Search ................................. 433/172, 173, 433/174, 175, 176

(56) References Cited

U.S. PATENT DOCUMENTS

| | | | |
|---|---|---|---|
| 5,094,618 | * 3/1992 | Sullivan | 433/175 |
| 5,194,000 | * 3/1993 | Dury | 433/173 |
| 5,195,892 | 3/1993 | Gersberg | 433/174 |
| 5,269,686 | 12/1993 | James | 433/174 |
| 5,316,476 | 5/1994 | Krauser | 433/173 |
| 5,366,374 | * 11/1994 | Vlassis | 433/173 |
| 5,449,291 | 9/1995 | Lueschen et al | 433/173 |
| 5,601,429 | 2/1997 | Blacklock | 433/174 |
| 5,676,545 | 4/1996 | Jones | 433/165 |
| 5,762,499 | 6/1996 | Dard et al. | 433/173 |

* cited by examiner

Primary Examiner—John J. Wilson
(74) Attorney, Agent, or Firm—Charles F. Reidelbach, Jr.; Higgs, Fletcher & Mack LLP

(57) ABSTRACT

A dental implant has a body with a press fit diameter fit into a hole drilled into a patient's jaw bone, and having a helical groove machined into the body diameter to improve the rate of growth of bone tissue thereinto to securely lock the implant in position. A shallow height oppositely wound helical thread may be added to increase the holding force upon initial fitting of the implant. The shallow height and long pitch of the thread produces only minimal stress of the surrounding bone tissue to insure long term retention.

8 Claims, 2 Drawing Sheets

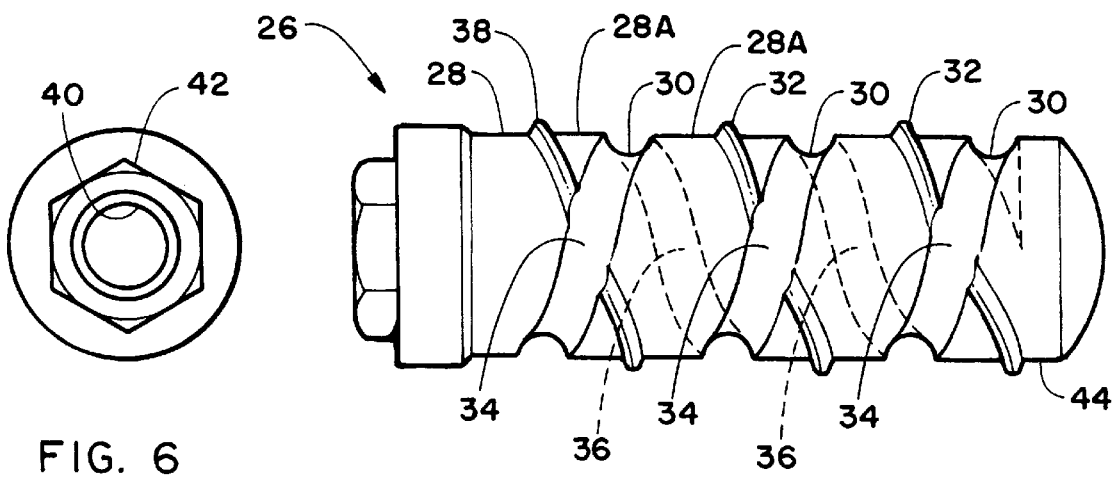
FIG. 6
FIG. 4
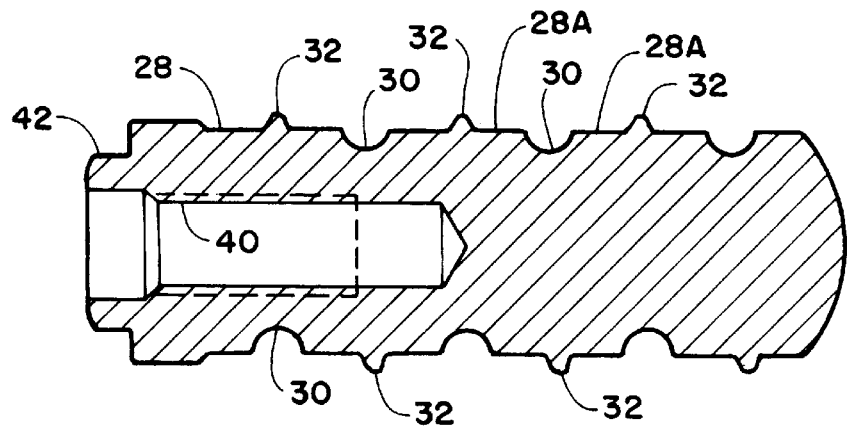
FIG. 5
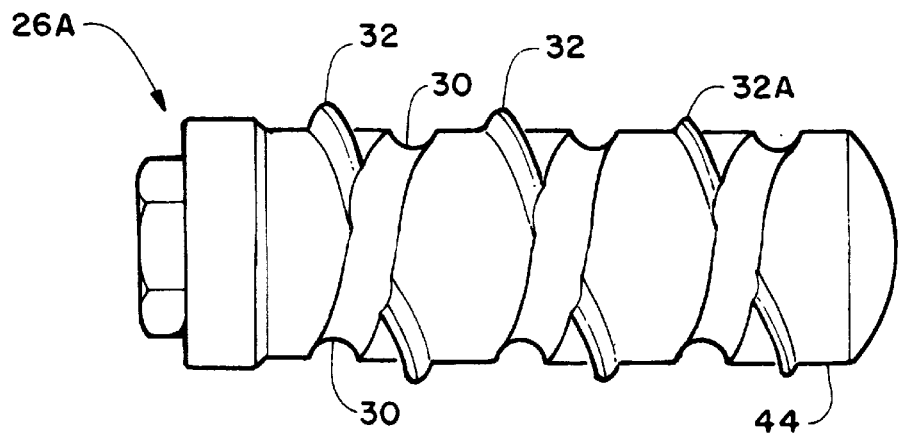
FIG. 7

HYBRID PRESS FIT-THREADED DENTAL IMPLANT

BACKGROUND OF THE INVENTION

This invention concerns a dental implant used as an artificial tooth root for holding a dental prostheses.

Dental implant typically comprises an elongated pin inserted into a hole drilled into the bone beneath a patient's gum tissue. The implants have taken two basic forms, a smooth cylindrical form which is press fit into the drilled hole and bonded to the osseous tissues to be held securely; and, a threaded form which is rotated into the hole which is suitably prepared by special bone tapping techniques.

The geometry of a threaded implant is such that it is immediately securely interlocked with the surrounding bone, the thread form when advanced into the hole creates excessive stresses in the bone tissue, which can cause the bone tissue to react and recede over time, leading to a loss of securement of the implant.

A threaded hole in the top of the implant is used for attachment of the prosthesis to the implant, and removal of a threaded attachment can sometimes result in loosening of the implant by unintended unscrewing of the implant threads when the attachment is loosened.

The press fit cylindrical form of the implant is simpler to install and has more bone attachment due to the absence of stress risers, but is less securely held in the bone tissue at the time that the implant is first driven into the hole since there is no positive mechanical interlock. The threaded form also has the advantage of having a greater surface area in contact with the bone, at least initially, to further increase the bonding forces.

Variations of these two basic forms have been devised, including a threaded form with the addition of a long pitch helical groove and through holes for receiving bone fragments packed into the groove to promote the growth of bone tissue into the groove for increased long term holding ability for the implant, as described in U.S. Pat. No. 5,676,545 issued on Oct. 14, 1997 for a "Method and Apparatus for Implantation".

U.S. Pat. No. 5,762,499 issued on Jun. 9, 1998 for a "Dental Root Implant" describes a press fit geometry in which the implant body is tapered and has circumferential grooves for receiving bone growth. U.S. Pat. No. 5,195,892 issued on May 23, 1993 for a "Bone-Integrated Dental Implant System" describes longitudinal grooves in the implant sides to promote interlocking bone growth.

U.S. Pat. No. 5,269,686 issued on Dec. 14, 1993 for a "Threaded Drivable Dental Implant" describes a long pitch rounded thread on an implant body which is drivable in the drilled hole and which resists loosening when an attachment screw is removed.

It is the object of the present invention to provide a dental implant which has the advantages of both the press fit and threaded forms while minimizing the disadvantages of each.

SUMMARY OF THE INVENTION

The above object and others which will become apparent upon a reading of the following specification and claims are achieved by a hybrid form of implant, having a smooth cylindrical body sized to be press fit in a drilled hole.

In a first form, a long pitched helical groove is recessed into the smooth cylindrical surface of the implant body. The groove shape promotes rapid bone growth into the groove and the helical shape creates a slight threaded retention as the adjacent bone tissue will protrude slightly into the groove under the pressure of the press fit of the implant.

In the second form, a very shallow height, long pitch thread is added, projecting from the cylindrical surface of the body of the implant, having an opposite helix angle from the helical groove turns but of approximately the same long pitch. The thread turns are interposed between the groove turns so as to cross the groove turns at diametrically opposite points on the implant body. Segments of the thread are removed in the areas where the thread turns cross the grooves to create a flattened shape similar to the oval shape of a natural tooth root.

The very shallow height thread can be easily forced into the surrounding bone tissue as the body is advanced into the drilled hole, with displaced bone fragments guided into the groove. The thread turns increase the retention forces upon initially fitting of the implant. The shallowness of the threads obviates the need for any special hole preparation and avoids imposition of significant stress on the bone tissue to insure long term secure retention of the implant.

In a variation of the second form, the height of the shallow thread is tapered down towards the implant forward or tip end, to more gradually cut into the bone tissue as the implant is advanced into the predrilled hole.

DESCRIPTION OF THE DRAWINGS

FIG. 4 is a side view of a second form of the dental implant according to the invention.

FIG. 5 is a sectional view of the dental implant shown in FIG. 4.

FIG. 6 is an end view of the dental implant shown in FIGS. 4 and 5.

FIG. 7 is a side view of a variation of the form of the dental implant shown in FIGS. 4–6.

DETAILED DESCRIPTION

In the following detailed description, certain specific terminology will be employed for the sake of clarity and a particular embodiment described in accordance with the requirements of 35 USC 112, but it is to be understood that the same is not intended to be limiting and should not be so construed inasmuch as the invention is capable of taking many forms and variations within the scope of the appended claims.

Figure 3:
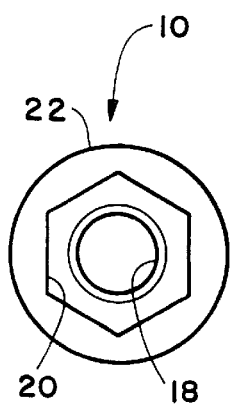
FIG. 3 is an end view of the dental implant shown in FIGS. 1 and 2.
Figure 1:
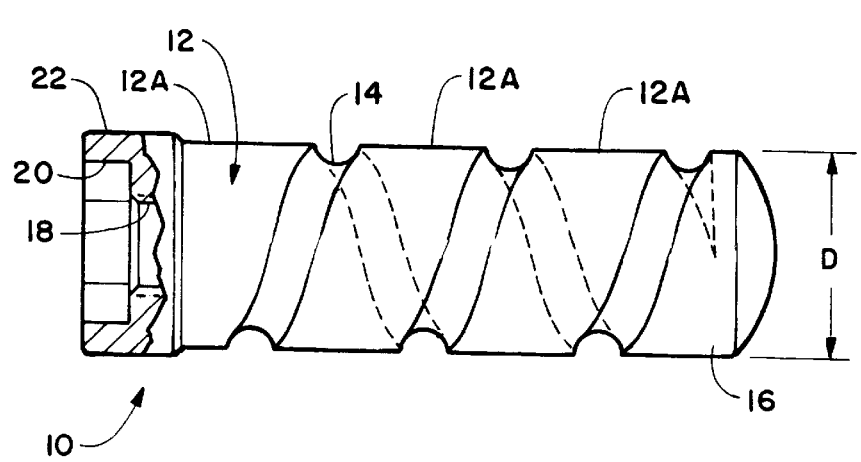
FIG. 1 is a side view of a first form of the dental implant according to the present invention.
Figure 2:
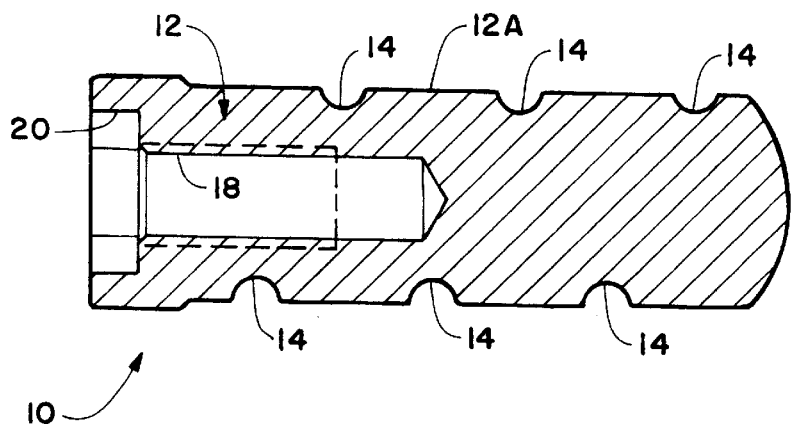
FIG. 2 is a sectional view of the dental implant shown in FIG. 1.

Referring to the Drawings, FIGS. 1–3 show a dental implant 10 according to the simplest form of the invention. An implant body 12 is formed with a cylindrical surface 12A of a diameter D sized to be press fit into a hole drilled into the patient's jaw bone. A long pitched helical groove 14 is machined into the body 12, with the turns widely spaced so that the majority of the length of the body 12 is constituted by the cylindrical surface 12A. The groove is arcuate in section and gently curved due to the long pitch.

A lead section 16 is of a slightly smaller diameter, i.e., 0.002 inches smaller than the cylindrical surface 12A, to allow the implant to be partially introduced into the drilled hole prior to driving the implant to its fully seated position.

A threaded longitudinal hole 18 is formed into the rear end of the implant 10 for receiving an attachment screw for mounting a prosthesis, in the well known manner.

A hexagonal wrenching counterbore 20 is formed into a slightly enlarged rear end 22 for driving the implant and for providing an antirotation feature for holding the prosthetic in its proper orientation.

The presence of the long pitch helical groove 14 creates a slight threaded engagement when the body 12 is press fit for improved retention of the implant, since the bone tissue will protrude slightly into the groove 14. The groove 14, being a curved rounded shape and arcuate in section, promotes the growth of bone tissue into the groove 14 for permanent, secure implant retention.

The implant 10 may be constructed of titanium (preferably 6AL4V), which term is meant to encompass both titanium and titanium alloys, and is grit blasted to smooth the corners and edges.

The groove is relatively wide (typically 0.029) inches) and shallow (typically 0.013 inches), varying slightly relative to the diameter of the implant.

FIGS. 4–6 show a second form of a dental implant 26 according to the invention which includes a body portion 28 formed with a cylindrical surface 28A of a diameter sized to be press fit into a hole drilled into bone tissue.

As in the above embodiment, a shallow long pitch helical groove 30 is machined into the cylindrical surface 28A, leaving the cylindrical surface 28A mostly uninterrupted to predominate the total exterior area of the body portion 28.

A very shallow height, long pitch helical thread 32 is also formed projecting above the surface 28A, of an opposite helix angle from turns of the groove 30. The turns of the thread 32 are disposed intermediate the turns of the groove 30. When the groove 30 is machined, the thread 32 is eliminated in the crossing areas 34, 36, creating a flattened shape in section, roughly approximately the oval shape of a natural tooth root.

The thread 32 preferably has a truncated crest 38 to form an outer flat about 0.005 inches wide, and may have a flank angle of approximately 60°, and a height of 0.011 inches such as to not displace bone tissue to a significant extent. This is compared to a typical body diameter D of 0.153 inches. The long pitch of the thread may be approximately 0.133 inches for implant lengths on the order of 10–18 mm.

The thread 32 is not fully formed so that large gaps exist between each turn, such gaps defined by the cylindrical press fit surfaces 28A. The axial length of these surfaces 28A is much greater than the width of the thread 32.

Such low height, long pitch thread does not create appreciable stress on the bone tissue, such that the implant retains a high degree of attachment.

The counter wound relationship of the groove 30 and thread 32 causes bone fragments displaced by the thread 32 to be pushed into the groove 30, allowing the implant to be advanced into the predrilled hole. The thread helix is also longer in pitch than the threads in a threaded hole 40 used for receiving an attachment screw for the prosthetic (not shown), so that loosening of the attachment screw does not cause loosening of the implant.

The thread 32 provides an immediate mechanical holding force upon driving of the implant into position, but without the time-consuming special hole preparation required of full thread implants, or the stress rising effect of those threads on the surrounding bone tissue.

The threaded hole 40 is machined into the rear end of the implant 26 for mounting the prosthetic (not shown). An external hexagonal antirotation feature 42 is also provided as per conventional practice.

A smaller diameter end at the front allows initial proper positioning of the implant 26 in the drilled hole.

FIG. 7 shows a modified version, in which the forward turns 32A of the thread 32 are of gradually reducing height and outside diameter to more gradually move the thread 32 into the bone tissue surrounding the predrilled hole.

What is claimed is:

1. An improved dental implant for providing a mounting for a prosthetic of a type including:

an elongated implate body having a main cylindrical portion, a forward end and a rear end, the improvement comprising:

said main portion having a helical groove formed therein of a long pitch helix angle establishing intermediate cylindrical surfaces in between turns of said helical groove, said cylindrical surfaces forming a substantial portion of the axial length of said main portion of said body; and a low height, long pitch, helical thread formed extending radially outward from said cylindrical portion and located intermediate said helical groove.

2. The dental implant of claim 1 wherein said implant is constructed of a material comprised of titanium.

3. The dental implant of claim 1 further including a reduced diameter portion at said forward end.

4. The dental implant of claim 1 wherein said helical thread is wound with an opposing helix angle from said helix angle of said groove turns.

5. The dental implant according to claim 4 wherein said thread turns are interrupted in areas crossing said groove turns.

6. The dental implant according to claim 1 wherein said cylindrical areas are substantially greater in axial extent than either of said thread turns or said groove turns.

7. The dental implant according to claim 1 wherein said thread is of gradually reduced height approaching said forward end.

8. The dental implant according to claim 1 wherein said thread has a flattened crest and of a height above said cylindrical surface on the order of 0.011 inches for a body diameter on the order of 0.153 inches.

* * * * *